(12) United States Patent
Dunne et al.

(10) Patent No.: US 8,412,490 B2
(45) Date of Patent: Apr. 2, 2013

(54) METHODS AND SYSTEMS FOR STRUCTURAL HEALTH MONITORING

(75) Inventors: James P. Dunne, Ballwin, MO (US); Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 300 days.

(21) Appl. No.: 12/847,141

(22) Filed: Jul. 30, 2010

(65) Prior Publication Data

US 2012/0029877 A1    Feb. 2, 2012

(51) Int. Cl.
*G06F 15/00* (2006.01)
(52) U.S. Cl. .................................................... 702/188
(58) Field of Classification Search ............ 702/188, 702/182; 73/587, 579
See application file for complete search history.

(56) References Cited

U.S. PATENT DOCUMENTS

| 6,006,163 | A  | 12/1999 | Lichtenwalner et al. |
| 7,024,315 | B2 | 4/2006  | Giurgiutiu |
| 7,426,447 | B2 | 9/2008  | Pado |
| 7,672,793 | B2 | 3/2010  | Beard |
| 7,734,429 | B2 | 6/2010  | Pado |
| 2007/0018083 | A1 | 1/2007 | Kumar et al. |
| 2007/0034009 | A1 | 2/2007 | Pado |
| 2009/0083004 | A1* | 3/2009 | Ihn et al. .................. 702/189 |

FOREIGN PATENT DOCUMENTS

| DE | 4240600 C1 | 9/1994 |
| GB | 2451959 A | 2/2009 |
| GB | 2453196 A | 4/2009 |
| WO | 2010115022 A2 | 10/2010 |
| WO | 2011007249 A1 | 1/2011 |

OTHER PUBLICATIONS

Combined Search and Examination Report of GB1111332.1; Aug. 30, 2011; 7 pages.

* cited by examiner

*Primary Examiner* — Bryan Bui
(74) *Attorney, Agent, or Firm* — Armstrong Teasdale LLP

(57) ABSTRACT

Methods and systems are provided for obtaining structural health data for evaluating a structural health of a component. A transducer detects a first signal representative of a signal transmitted through at least a portion of the component. An estimated signal for a remote transducer is determined based on at least the first signal and a transfer function.

15 Claims, 4 Drawing Sheets

METHODS AND SYSTEMS FOR STRUCTURAL HEALTH MONITORING

BACKGROUND

The present disclosure relates to assessing the integrity of a structure and, more particularly, to methods and systems for structural health monitoring.

Known structures may be inspected to determine whether the structure has developed any weaknesses and/or conditions that could potentially impact the structural health of the structure. For example, at least some known structures are subjected to stresses and/or tensions that could lead to a weakened area, such as a crack in the structure. To determine the existence of such conditions and potentially extend the life of the structure, structural health monitoring (SHM) systems may be used.

Some known SHM systems include at least one transducer positioned to cause a signal to be transmitted at least partially through the structure. Due to structural characteristics and/or material properties of the structure, the signals passing through the structure are attenuated. Another transducer detects the attenuated signal and the signals output by such transducers are used to evaluate the structural health of the structure.

Typically, not all signals output by the detecting transducer are usable to evaluate structural health. For example, at least some of the signals output by the detecting transducer may have relatively low signal-to-noise ratio (SNR). Discarding such signals, however, results in a loss of information related to the structure. As a consequence, the accuracy and/or completeness of the structural health evaluation may be adversely impacted. To facilitate reducing a likelihood for at least some transmitted signals being disrupted by noise and/or other interferences, at least some SHM systems have a relatively high transducer density. High-transducer-density SHM systems, however, are typically associated with an increased cost, weight, wiring, need for computer resources, and/or likelihood of failure.

BRIEF DESCRIPTION

In one aspect, a method is provided for obtaining structural health data for evaluating a structural health of a component. The method includes detecting a first signal representative of a signal transmitted through at least a portion of the component. An estimated signal is determined for a remote transducer based on at least the first signal and a transfer function associated with the remote transducer.

In another aspect, an array of transducers is provided for use in obtaining structural health data for evaluating a structural health of a component. The array includes a first transducer, a second transducer, and a third transducer. The first transducer is configured to transmit a signal through at least a portion of the component. The second transducer is configured to detect a first signal representative of the signal transmitted through at least the portion of the component. An estimated signal for the third transducer is determined based on at least the first signal and a transfer function associated with the third transducer.

In yet another aspect, a structural health monitoring system is provided for use in obtaining structural health data for evaluating a structural health of a component. The system includes a first transducer, a second transducer, and a computing system. The first transducer is configured to transmit a signal through at least a portion of the component. The second transducer is configured to detect a first signal representative of the signal transmitted through at least the portion of the component. The computing system is programmed to determine an estimated signal for a remote transducer based on at least the first signal and a transfer function associated with the remote transducer.

The features, functions, and advantages that have been discussed can be achieved independently in various embodiments of the present invention or may be combined in yet other embodiments further details of which can be seen with reference to the following description and drawings.

DETAILED DESCRIPTION

The subject matter described herein relates to methods and systems for structural health monitoring. In one embodiment, a signal is transmitted through at least a portion of a component. A first signal representative of the signal is detected, and an estimated signal is determined for a remote transducer based on at least the first signal and a transfer function associated with the remote transducer. In such an embodiment, determining the estimated signal for the remote transducer enables extending usable signal paths in a structural health monitoring application. Although the present disclosure is described in the context of assessing the integrity of a structure and, more specifically, described in the context of structural health monitoring of aircraft structures, it should be understood that the present disclosure may be used in many other contexts in which it is desirable to increase a usability of a signal transmitted through at least a portion of a component.

Technical effects of the methods, systems, and computer-readable media described herein include at least one of: (a) determine a desired distance between adjacent transducers; (b) detect a first signal representative of a signal transmitted through at least the portion of a component; (c) scale the signal transmitted through at least the portion of the component; (d) determine a transfer function; and (e) determine an estimated signal for a remote transducer based on at least the first signal and the transfer function.

As used herein, an element or step recited in the singular and proceeded with the word "a" or "an" should be understood as not excluding plural elements or steps unless such exclusion is explicitly recited. Furthermore, references to "one embodiment" of the present invention are not intended to be interpreted as excluding the existence of additional embodiments that also incorporate the recited features.

Figure 1:
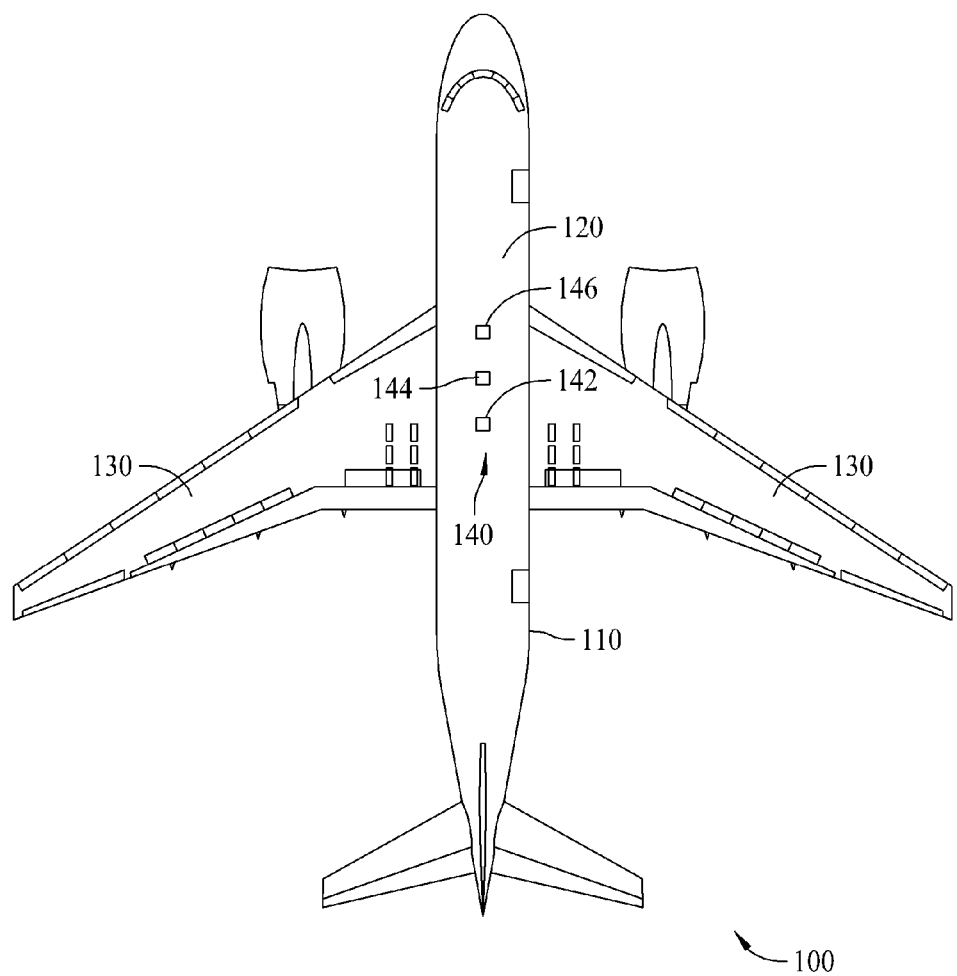
FIG. 1 is a plan view of an exemplary aircraft.

FIG. 1 is a plan view of an exemplary aircraft 100 including a body 110. In the exemplary embodiment, body 110 includes a fuselage 120 and a pair of wings 130. In the exemplary embodiment, an array of transducers 140 including at least a first transducer 142, a second transducer 144, and a third transducer 146 is coupled to fuselage 120. As described above, a "transducer" is capable of transmitting and/or detecting a signal. For example, any combination of transducers 142, 144, and/or 146 may be piezoelectric transducers.

In the exemplary embodiment, at least one transducer 142, 144, 146 imparts energy into body 110, and at least one transducer 142, 144, 146 senses and/or detects a response to the energy imparted into body 110. Although FIG. 1 illustrates three transducers, it should be understood that any number of transducers may be used that enables a structural health monitoring system (not shown in FIG. 1) to function as described herein. Furthermore, array 140 is not limited to only being positioned relative to aircraft 100 as illustrated.

Figure 2:
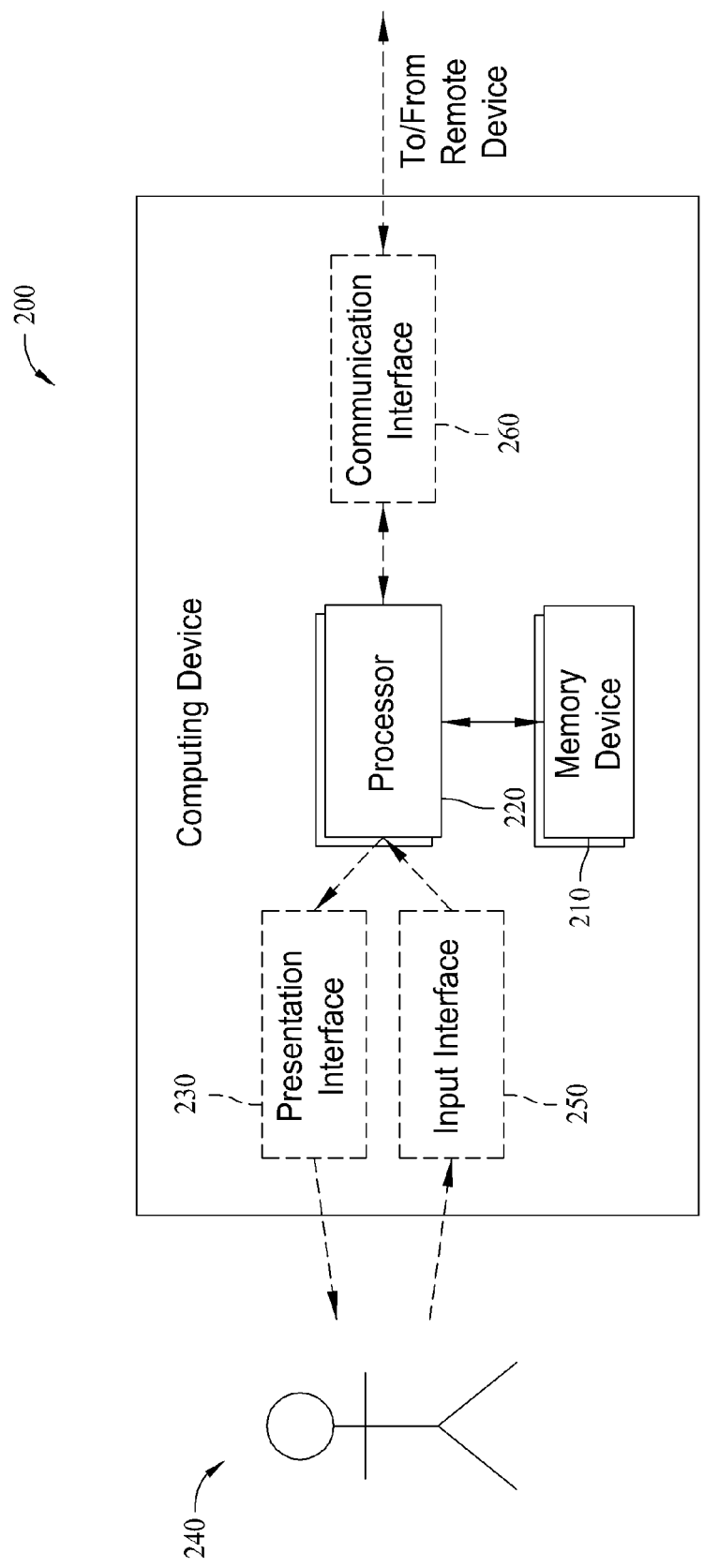
FIG. 2 is a block diagram of an exemplary computing system.

FIG. 2 is a block diagram of an exemplary computing system 200 that may be used to assess a structural integrity of aircraft 100. Computing system 200, as described herein, implements a structural health monitoring (SHM) algorithm to increase a usability of signal transfer paths.

In the exemplary embodiment, computing system 200 includes a memory device 210 and a processor 220 that is coupled to memory device 210 for executing programmed instructions stored therein. Processor 220 may include one or more processing units, for example, in a multi-core configuration. In one embodiment, executable instructions and/or SHM data are stored in memory device 210. Computing system 200 is programmable to perform one or more operations described herein by programming memory device 210 and/or processor 220. For example, processor 220 may be programmed by encoding an operation as one or more executable instructions and providing the executable instructions in memory device 210.

Processor 220 may include, but is not limited to only including, a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor that is capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

Memory device 210, as described herein, is one or more devices that enable information such as executable instructions and/or other data to be stored and retrieved. Memory device 210 may include one or more computer readable media, such as, without limitation, dynamic random access memory (DRAM), static random access memory (SRAM), a solid state disk, and/or a hard disk. Memory device 210 may be configured to store, without limitation, executable instructions, configuration data, SHM data, and/or any other type of data.

In the exemplary embodiment, computing system 200 includes a presentation interface 230 that is coupled to processor 220. Presentation interface 230 displays, presents, and/or otherwise outputs information. Such information includes, but is not limited to, configuration data, SHM data, and/or any other type of data to a user 240. For example, presentation interface 230 may include a display adapter (not shown in FIG. 2) that is coupled to a display device, such as a cathode ray tube (CRT), a liquid crystal display (LCD), a light-emitting diode (LED) display, an organic LED (OLED) display, and/or an "electronic ink" display. In some embodiments, presentation interface 230 includes more than one display device. In addition, or in the alternative, presentation interface 230 may include a printer.

In the exemplary embodiment, computing system 200 includes an input interface 250 that receives input from user 240. For example, input interface 250 may be configured to receive an indication of configuration data, SHM data, and/or any other type of data suitable for use with the methods and systems described herein. As described in further detail below, computing system 200 uses the received input to develop and/or implement a software application. In the exemplary embodiment, input interface 250 is coupled to processor 220 and may include, for example, a keyboard, a pointing device, a mouse, a stylus, a touch sensitive panel (e.g., a touch pad or a touch screen), a gyroscope, an accelerometer, a position detector, and/or an audio input interface. A single component, such as a touch screen, may function as both a display device of presentation interface 230 and as input interface 250.

In the exemplary embodiment, computing system 200 includes a communication interface 260 coupled to memory device 210 and/or processor 220. Communication interface 260 is coupled in communication with a remote device, such as transducer 142, 144, 146, and/or another computing system 200. For example, communication interface 260 may include, without limitation, a wired network adapter, a wireless network adapter, and/or a mobile telecommunications adapter.

Figure 3:
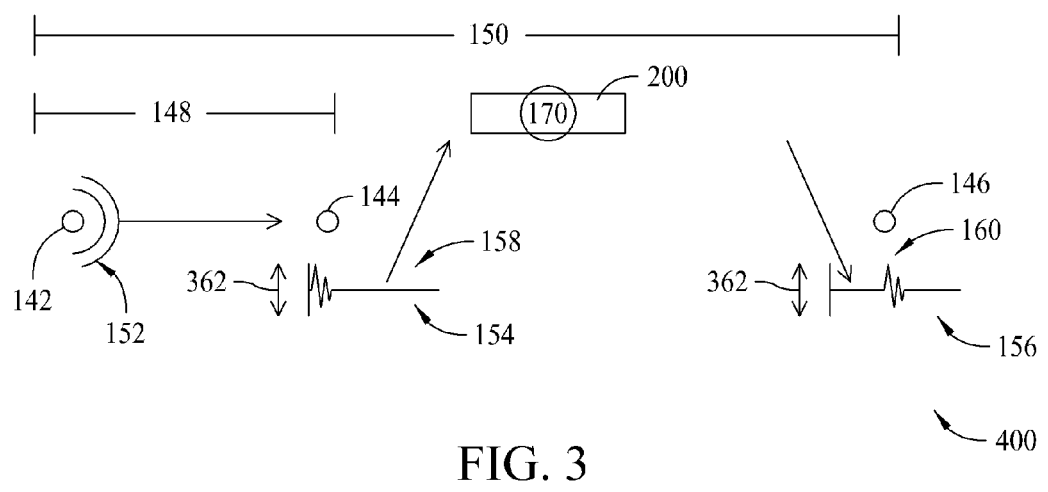
FIG. 3 is a schematic illustration of an exemplary structural health monitoring system that may be used with the computing system shown in FIG. 2.

FIG. 3 is a schematic illustration of an exemplary SHM system 400. In the exemplary embodiment, SHM system 400 includes first transducer 142, second transducer 144, and third transducer 146 (also shown in FIG. 1). Notably, SHM system 400 may include any quantity of transducers that enables SHM system 400 to function as described herein. In the exemplary embodiment, first transducer 142 and second transducer 144 are spaced a first distance 148 apart, and first transducer 142 and third transducer 146 are spaced a second distance 150 apart that is greater than first distance 148.

In the exemplary embodiment, first transducer 142 transmits a signal 152 through at least a portion of a component, such as aircraft 100. Signal 152 attenuates as it traverses through a medium, such as aircraft 100. As such, second transducer 144 detects a first signal 154 that is representative of signal 152. In the exemplary embodiment, first signal 154 has a first SNR 158. Additionally, third transducer 146 may detect a signal that is representative of signal 152 (not shown).

More specifically, in the exemplary embodiment, at or beyond a given distance from first transducer 142, a signal representative of signal 152 attenuates to a level such that its signal-to-noise ratio (SNR) is below a predetermined threshold 362. In one embodiment, threshold 362 can be defined at any value or range of values between approximately 7 and approximately 13 decibels (dB). In another embodiment, threshold 362 can be any value or range of values from approximately 5 to approximately 20 dB. In yet another embodiment, threshold 362 can vary significantly below approximately 5 dB and significantly above approximately 20 dB.

Typically, such signals at or beyond the given distance are undesirably compromised by noise and, thus, are dispensed and/or disregarded by SHM system 400. For example, in the exemplary embodiment, first signal 154 has a first SNR 158 that is above threshold 362. Because signal 152 increasingly attenuates as it travels through aircraft 100 and/or is potentially disrupted by noise and/or other interferences as signal 152 traverses through aircraft 100, third transducer 146 typically detects a signal that has a SNR than is less than first SNR 158 and at or below threshold 362. In one embodiment, an attenuation of signal 152 may be directional and may be usable at varying distances in different directions.

To facilitate providing usable SHM for third transducer 146, computing system 200 determines an estimated signal 156 for third transducer 146 based on first signal 154 and/or a transfer function 170, described in further detail below. More specifically, in the exemplary embodiment, data representative of first signal 154 is transmitted to computing system 200. If computing system 200 determines first SNR 158 to be above threshold 362, computing system 200 determines estimated signal 156 for third transducer 146. Because estimated signal 156 is a projection of signal 152 and/or first signal 154, in the exemplary embodiment, estimated signal 156 may be determined to have a second SNR 160 that is above threshold 362. In the exemplary embodiment, data representative of estimated signal 156 may be transmitted to third transducer 146. If first SNR 158 is at or below threshold 362, signal 152 may be scaled and/or retransmitted to increase first SNR 158 above threshold 362.

To determine transfer function 170, in the exemplary embodiment, second transducer 144 transmits a new signal (not shown) through at least a second portion of aircraft 100. Because the new signal attenuates as it traverses through a medium, such as aircraft 100, third transducer 146 detects a second signal (not shown) that is representative of the new signal. Data representative of the new signal and/or the second signal is transmitted to computing system 200.

In the exemplary embodiment, computing system 200 is programmed to determine transfer function 170 based on a strength of the new signal transmitted from second transducer 144 and/or a strength of the second signal detected at third transducer 146. As such, transfer function 170 is representative of a relationship between second transducer 144 and third transducer 146. A similar method using first transducer 142 and second transducer 144 may be used to determine a second transfer function (not shown) that represents a relationship between first transducer 142 and second transducer 144. Notably, any suitable number of transfer functions may be determined to enable SHM system 400 to function as described herein.

In the exemplary embodiment, computing system 200 may be programmed to determine a structural health parameter based on first signal 154 and/or estimated signal 156 to assess the integrity of aircraft 100. In the exemplary embodiment, at least one characteristic and/or feature (not shown) may be extracted from first signal 154 and/or estimated signal 156 to identify damage, weakness, and/or any other condition that could potentially impact the structural health of aircraft 100. Metrics of structural health based upon such features are widely known and available to one skilled in the art, and can be used to ascertain the health of the structure. For example, such features may include, but are not limited to, time-of-flight, attenuation, mode conversion, and/or phase shift.

In the exemplary embodiment, computing system 200 may be programmed to determine a desired distance between adjacent transducers to establish a desired transducer density for array 140 and/or to position transducer 142, 144, and/or 146. The desired distance between adjacent transducers may be based on a transfer function, transmitted signal, detected signal, and/or threshold. In the exemplary embodiment, first distance 148 may be determined based on first SNR 158 and/or threshold 362, and second distance 150 may be determined based on first SNR 158, transfer function 170 and/or threshold 362.

Figure 4:
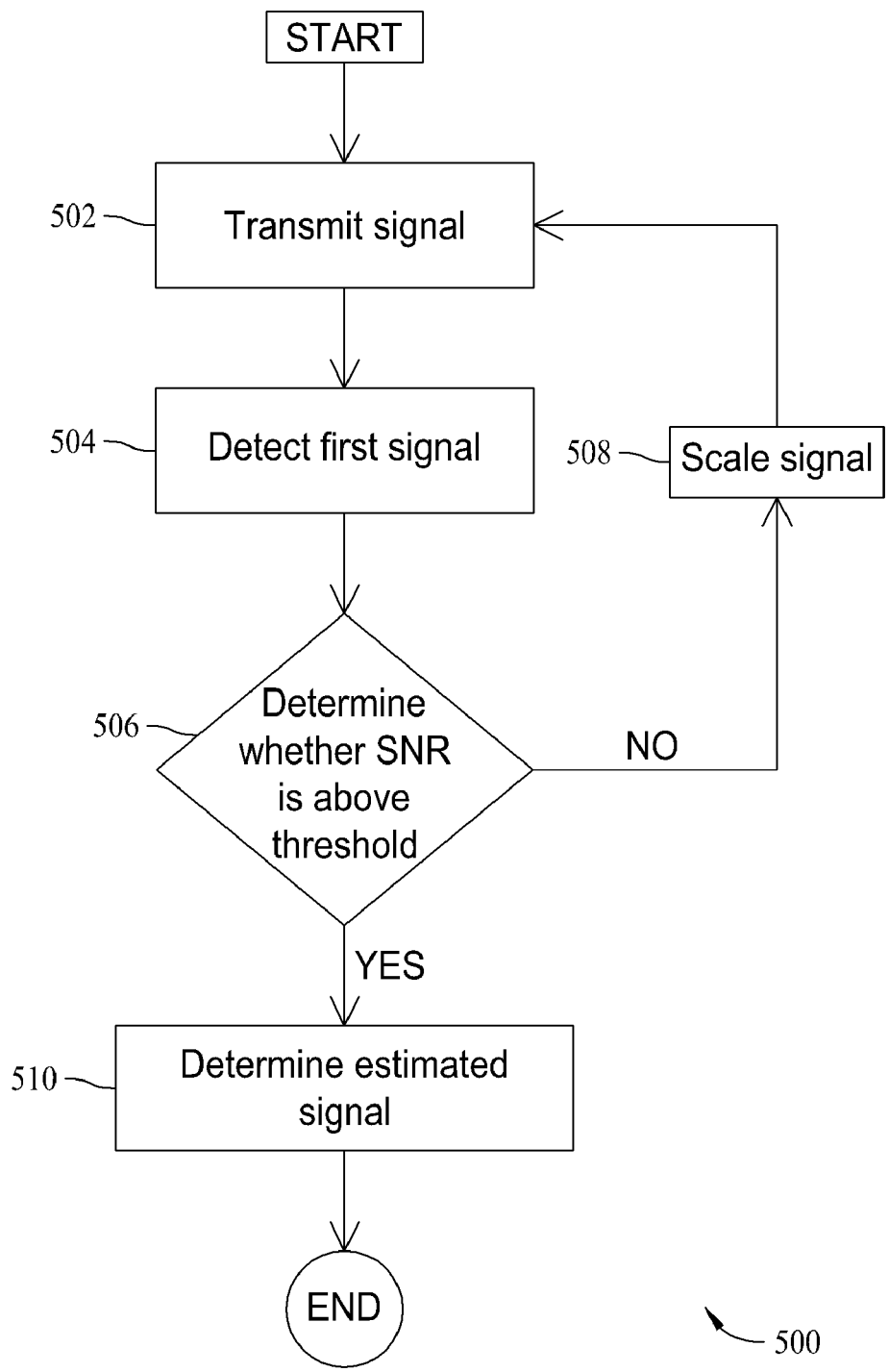
FIG. 4 is a flow chart illustrating an exemplary method for obtaining structural health data using the structural health monitoring system shown in FIG. 4.

FIG. 4 is a flow chart illustrating an exemplary method 500 for increasing a usability of a signal transmitted using SHM system 400. Initially, first signal 152 is transmitted 502 through at least a portion of aircraft 100, and first signal 154, which is representative of an attenuated signal 152, is detected 504.

In the exemplary embodiment, data representative of first signal 154 is transmitted to computing system 200, which determines 506 whether first SNR 158 is above threshold 362. If SNR ratio 158 is at or below threshold, then computing system 200 transmits instructions for signal 152 to be scaled 508, retransmitted 502, and redetected 504 until first SNR 158 is above threshold 362.

When SNR ratio 158 is above threshold, first signal 152 is suitable for use, and computing system 200 determines 510 estimated signal 156 for third transducer 146. In the exemplary embodiment, estimated signal 156 is based on first signal 154 and/or transfer function 170.

The embodiments described herein facilitate inspecting a structure to determine whether any weakness and/or condition that could potentially impact the structural health of the structure has developed. More specifically, the embodiments described herein enable increasing a usability of a signal transmitted through a medium. As such, the embodiments described herein provide means for identifying, localizing, and/or sizing such weaknesses and/or conditions. Additionally, the exemplary methods and systems facilitate reducing a transducer density of an SHM system and, thus, an associated overhead including cost, weight, wiring, need for computer resources, and/or likelihood of failure.

The exemplary systems and methods are not limited to the specific embodiments described herein, but rather, components of each system and/or steps of each method may be utilized independently and separately from other components and/or method steps described herein. Each component and each method step may also be used in combination with other components and/or method steps.

This written description uses examples to disclose certain embodiments of the invention, including the best mode, and also to enable any person skilled in the art to practice those certain embodiments, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for obtaining structural health data for evaluating a structural health of a component, said method comprising:
   detecting, at a transducer, a first signal representative of a signal transmitted through at least a portion of the component;
   determining whether the first signal has a signal-to-noise ratio below a predetermined threshold;
   scaling, at a computing device, the signal transmitted through at least the portion of the component if the signal-to-noise ratio is below the predetermined threshold such that the signal-to-noise ratio is scaled to be above the predetermined threshold; and
   determining, at the computing device, an estimated signal for a remote transducer based on at least the first signal and a predetermined transfer function representative of a relationship between the transducer and the remote transducer.

2. A method in accordance with claim 1, wherein determining an estimated signal further comprises:

transmitting a new signal through a second portion of the component;

detecting a second signal representative of the new signal transmitted through at least the second portion of the component; and determining the transfer function based on at least the new signal transmitted through at least the second portion of the component and the second signal.

3. A method in accordance with claim 1, wherein scaling the signal further comprises determining a second transfer function based on the signal transmitted through at least the portion of the component and the first signal.

4. A method in accordance with claim 1 further comprising determining a desired distance between adjacent transducers based on at least one of the transfer function, the signal-to-noise ratio of the first signal, and the predetermined threshold.

5. An array of transducers for use in obtaining structural health data for evaluating a structural health of a component, said array comprising:

a first transducer configured to transmit a signal through at least a portion of the component and scale the signal such that a signal-to-noise ratio of the first signal is above a predetermined threshold;

a second transducer configured to detect a first signal representative of the signal transmitted through at least the portion of the component; and a third transducer in a predetermined position such that a computing system is configured to determine an estimated signal for the third transducer based on at least the first signal and a predetermined transfer function representative of a relationship between the second transducer and the third transducer.

6. An array in accordance with claim 5, wherein the second transducer is further configured to transmit a new signal through a second portion of the component, and the third transducer is further configured to detect a second signal representative of the new signal transmitted through at least the second portion of the component, the transfer function determined based on at least the new signal transmitted through at least the second portion of the component and the second signal.

7. An array in accordance with claim 5, wherein the first transducer and the second transducer are positioned at a desired distance determined based on at least one of the signal-to-noise ratio of the first signal and the predetermined threshold.

8. An array in accordance with claim 5, wherein the second transducer and the third transducer are positioned at a desired distance determined based on at least one of the transfer function and the predetermined threshold.

9. An array in accordance with claim 5, wherein the first transducer and the third transducer are positioned at a desired distance determined based on at least one of the signal-to-noise ratio of the first signal, the transfer function, and the predetermined threshold.

10. A structural health monitoring system for use in obtaining structural health data for evaluating a structural health of a component, said system comprising:

a first transducer configured to transmit a signal through at least a portion of the component;

a second transducer configured to detect a first signal representative of the signal transmitted through at least the portion of the component;

a computing system programmed to determine whether the first signal has a signal-to-noise ratio below a predetermined threshold, scale the signal transmitted through at least the portion of the component if the signal-to-noise ratio is below the predetermined threshold such that the signal-to-noise ratio is scaled to be above the predetermined threshold, and determine an estimated signal for a remote transducer based on at least the first signal and a predetermined transfer function representative of a relationship between the second transducer and the remote transducer.

11. A structural health monitoring system in accordance with claim 10, wherein the second transducer is further configured to transmit a new signal through a second portion of the component, the remote transducer is configured to detect a second signal representative of the new signal transmitted through at least the second portion of the component, and the computing system is further programmed to determine the transfer function based on at least the new signal transmitted through at least the second portion of the component and the second signal.

12. A structural health monitoring system in accordance with claim 10, wherein the computing system is further programmed to determine a second transfer function based on the signal transmitted through at least the portion of the component and the first signal.

13. A structural health monitoring system in accordance with claim 10, wherein the computing system is further programmed to determine a desired distance between the first transducer and the second transducer based on at least one of the signal-to-noise ratio of the first signal and the predetermined threshold.

14. A structural health monitoring system in accordance with claim 10, wherein the computing system is further programmed to determine a desired distance between the second transducer and the remote transducer based on at least one of the transfer function and the predetermined threshold.

15. A structural health monitoring system in accordance with claim 10, wherein the computing system is further programmed to determine a desired distance between the first transducer and the remote transducer based on at least one of the signal-to-noise ratio of the first signal, the transfer function, and the predetermined threshold.

* * * * *